(12) United States Patent
Riesinger

(10) Patent No.: US 9,302,033 B2
(45) Date of Patent: Apr. 5, 2016

(54) WOUND TREATMENT DEVICE WITH ELASTICALLY DEFORMABLE VACUUM PRODUCING ELEMENT

(71) Applicant: Birgit Riesinger, Ostbevern (DE)

(72) Inventor: Birgit Riesinger, Ostbevern (DE)

(73) Assignee: BSN medical GmbH, Hamburg (DE)

( * ) Notice: Subject to any disclaimer, the term of this patent is extended or adjusted under 35 U.S.C. 154(b) by 0 days.

(21) Appl. No.: 14/053,558

(22) Filed: Oct. 14, 2013

(65) Prior Publication Data
US 2014/0039423 A1     Feb. 6, 2014

Related U.S. Application Data

(63) Continuation of application No. 12/096,264, filed as application No. PCT/EP2006/012041 on Dec. 14, 2006, now abandoned.

(30) Foreign Application Priority Data

Dec. 14, 2005   (DE) .................... 20 2005 019 670 U

(51) Int. Cl.
*A61M 1/00*    (2006.01)
*A61M 27/00*    (2006.01)
(Continued)

(52) U.S. Cl.
CPC .......... *A61M 1/0088* (2013.01); *A61F 13/0203* (2013.01); *A61F 13/0209* (2013.01); *A61M 1/0003* (2013.01); *A61M 1/009* (2014.02); *A61M 1/0009* (2013.01); *A61M 1/0011* (2013.01); *A61M 1/0072* (2014.02); *A61M 1/08* (2013.01); *A61B 19/42* (2013.01); *A61F 13/00068* (2013.01); *A61F 2013/0054* (2013.01);
(Continued)

(58) Field of Classification Search
CPC .......... A61F 13/0203; A61F 13/00068; A61F 2013/0017; A61F 2013/00174; A61F 2013/00536; A61F 2013/0054; A61F 13/0209; A61F 2013/00557; A61M 1/0088; A61M 1/0072; A61M 1/009; A61M 2205/075; A61M 27/00; A61M 35/003; A61M 1/08; A61M 1/0003; A61M 1/0066; A61B 19/42; A61B 17/085
See application file for complete search history.

(56) References Cited

U.S. PATENT DOCUMENTS 1,460,927 A * 7/1923 Thompson ............... A61H 7/00
                                                                      15/110
3,486,504 A   12/1969 Austin, Jr.
(Continued)

FOREIGN PATENT DOCUMENTS

DE      2953373 C2    12/1989
DE      19517669 A1   11/1996
(Continued)

*Primary Examiner* — Adam Marcetich
(74) *Attorney, Agent, or Firm* — Rankin, Hill & Clark LLP

(57) ABSTRACT

The invention relates to a wound treatment device with at least one elastically deformable vacuum-generating element which can be actuated directly by hand and which is arranged on and connected directly to a film-like wound-covering element that covers the wound chamber. The vacuum-generating element is a hollow body whose cavity, in the state with the device applied to the patient's body, communicates directly with the wound chamber via an opening formed on the wound-covering element. At least one absorption body that absorbs the wound secretions is positioned in the wound chamber and is surrounded by a finely porous sleeve that is permeable to liquid. The hollow body is provided with at least one valve.

20 Claims, 11 Drawing Sheets

(51) Int. Cl.
*A61M 1/08* (2006.01)
*A61F 13/02* (2006.01)
*A61F 13/00* (2006.01)
*A61B 19/00* (2006.01)

(52) U.S. Cl.
CPC .............. *A61F2013/00165* (2013.01); *A61F 2013/00536* (2013.01); *A61F 2013/00557* (2013.01); *A61M 2205/075* (2013.01)

(56) References Cited

U.S. PATENT DOCUMENTS

| | | | |
|---|---|---|---|
| 3,683,922 A | | 8/1972 | Cutter |
| 3,874,387 A | * | 4/1975 | Barbieri ............... A61B 17/085 128/888 |
| 4,382,441 A | | 5/1983 | Svedman |
| 4,465,062 A | * | 8/1984 | Versaggi et al. ............. 128/897 |
| 4,997,438 A | * | 3/1991 | Nipper ..................... A61F 5/30 606/201 |
| 5,139,023 A | | 8/1992 | Stanley et al. |
| 5,454,779 A | * | 10/1995 | Lurie ..................... A61H 31/00 601/43 |
| 5,549,584 A | | 8/1996 | Gross |
| 5,562,107 A | | 10/1996 | Lavender et al. |
| 5,589,256 A | * | 12/1996 | Hansen ............... A61F 13/0209 156/296 |
| 5,636,643 A | | 6/1997 | Argenta et al. |
| 5,759,570 A | | 6/1998 | Arnold |
| 6,174,306 B1 | | 1/2001 | Fleischmann |
| 6,234,980 B1 | | 5/2001 | Bell |
| 6,447,799 B1 | | 9/2002 | Ullman |
| 6,617,486 B1 | | 9/2003 | Murata |
| 6,656,147 B1 | | 12/2003 | Gertsek et al. |
| 6,685,681 B2 | | 2/2004 | Lockwood et al. |
| 6,855,133 B2 | | 2/2005 | Svedman |
| 2001/0029956 A1 | | 10/2001 | Argenta et al. |
| 2002/0111576 A1 | | 8/2002 | Greene et al. |
| 2003/0097864 A1 | | 5/2003 | Montes et al. |
| 2004/0033750 A1 | * | 2/2004 | Everett et al. ................. 442/381 |
| 2004/0054313 A1 | | 3/2004 | Molan |
| 2004/0064132 A1 | | 4/2004 | Boehringer et al. |
| 2005/0070835 A1 | * | 3/2005 | Joshi ................... A61M 1/0066 602/41 |
| 2005/0143697 A1 | | 6/2005 | Riesinger |
| 2005/0175649 A1 | | 8/2005 | Disalvo et al. |
| 2007/0167926 A1 | | 7/2007 | Blott et al. |
| 2008/0009812 A1 | | 1/2008 | Riesinger |
| 2008/0119802 A1 | | 5/2008 | Riesinger |

FOREIGN PATENT DOCUMENTS

| | | | |
|---|---|---|---|
| DE | 19844355 A1 | 4/2000 | |
| DE | 202004017052 U1 | 7/2005 | |
| DE | 202004018245 U1 | 8/2005 | |
| FR | 1163907 | 10/1958 | |
| FR | 1279632 A | * 12/1961 | ............. A61M 1/08 |

* cited by examiner

WOUND TREATMENT DEVICE WITH ELASTICALLY DEFORMABLE VACUUM PRODUCING ELEMENT

CROSS-REFERENCE TO RELATED APPLICATIONS

This application is a continuation of application Ser. No. 12/096,264, filed Jul. 31, 2008, which application was a U.S. National Stage of International Application No. PCT/EP2006/012041, filed Dec. 14, 2006, and claims priority to German Patent Application No. DE 20 2005 019 670.3, filed Dec. 14, 2005.

BACKGROUND OF INVENTION

1. Field of Invention

The invention concerns a wound treatment device with at least one elastically deformable vacuum producing element, which can be operated directly by hand, being arranged on a film-like wound cover element, covering the particular wound cavity, and being connected to the latter tubelessly.

2. Description of Related Art

A wound treatment device of the above mentioned kind is found in DE 198 44 355 A1. The vacuum producing element shown in FIG. 2 is glued directly to the wound cover film. The vacuum producing element is a bell-shaped hollow body, filled with a pre-compressed sponge, which swells up during the suction process only when a water-soluble plate located between the sponge and the wound surface dissolves. The pre-compressed sponge also presses against the entire inner surface of the hollow body. The compression and subsequent expanding of the sponge in the direction of the wound can also occur without a water-soluble plate if the sponge is compressed only when the bandage is put in place and the sponge is accommodated in the hollow body. The drawback in both instances is that the compressed sponge upon expanding presses against the sensitive wound surface.

The problem of the invention is to design an improved wound treatment device with vacuum producing element, integrated with the wound cover film, wherein the pre-compressed filling can be done away with.

BRIEF SUMMARY OF THE INVENTION

This problem is solved by a wound treatment device of this kind, wherein
the vacuum producing element is a hollow body, whose cavity in the condition placed on the patient's body is in direct contact with the wound cavity via an opening worked into the wound cover element, and
at least one absorption body to absorb the wound secretions is placed in the wound cavity, being surrounded by a fine-pore, liquid-permeable envelope.

The aim is to achieve a new kind of wound treatment device, in which the wound exudate is taken up by the absorption body, while at the same time the suction function is supported by a simplified vacuum system which can be activated by hand. The absorption body can be a sheet-like shape, whose final volume increases greatly in the course of the absorption process, without exerting a noteworthy pressure on the wound surface. However, if a pressure is to be exerted on the wound, one can at least resort to an additional absorption body, encased or not, which can be placed directly on the wound surface, i.e., underneath the mentioned flat absorption body. The additional absorption body can also take on the function of a trapping layer for the coarse, clumplike secretions. The absorption body can be placed dry or slightly pre-moistened on the wound surface.

The additional absorption body can be a perforated pouch containing absorbent particles, a shaped piece of foam plastic or fleece, possible with superabsorbent particles. Superabsorbing foam plastic beads can be poured into the pouch.

The encased absorption body can be one which is interspersed with superabsorbents. The envelope can have pores whose size does not greatly exceed that of the superabsorbing particles. In this way, the wound secretions sucked up remain inside the envelope until the absorption body is removed from the wound and help improve the climate of the wound space, i.e., maintain the moist surroundings. The wound exudate does not necessarily have to be taken away through an additional conduit, unless there is an excess of wound exudate.

The absorption body can be made from various medically safe materials, such as open-cell foam plastic, gel or textile. Preferably, it consists of at least one layer of a fleece-like textile material containing cellulose and having superabsorbent particles, which is easy to work and make ready. The absorption body can consist of or contain alginate fibers. It is expressly pointed out that the absorption body (or bodies) placed in the wound cavity or in the cavity of the hollow body is (are) not pre-compressed.

Finally, the shaped absorbing piece or the pouch with absorber particles contained therein can be placed directly on the wound, without having to use the mentioned encased sheet-like absorption body.

In order to kill germs, the encased absorption body and/or the additional absorption body of fleece or foam plastic or an anti-adhesive film element which can be placed directly on the wound can be provided with substances containing silver or copper, for example, in nanocrystalline form. As the anti-adhesive film element, one can use a perforated so-called wound spacer grid, which is arranged between the wound surface and the absorption body. Substances containing zinc are also possible, and can support the wound healing process.

Furthermore, the absorption body can contain carboxymethylcellulose, natural or synthetic hyaluronic acid, honey and/or its derivatives, propolis and/or pharmaceutically active plant extracts, such as Aloe vera.

The compressible hollow body can have any desired external shape, provided that it is connected tubelessly to the wound cover element and sits stable thereupon. The hollow body can have the shape of a prism, such as a cuboid. Preferably, the hollow body is configured as an elastically deformable solid of revolution, such as one made of elastomer. The hollow solid of revolution can be spherical, cylindrical or conical, but it can also have the shape of a pear or oval cylinder. An especially advantageous configuration of the hollow body is a cuboidal or somewhat cylindrical bellows, which can be deformed essentially only in one direction, say, perpendicular to the emplaced would cover element.

Preferably, the hollow body is joined to a circumferential flat collar, which can be joined to the wound cover element directly or via a cushion ring. The cushion ring can have a flat to round or toroidal cross section. The task of the cushion ring is to gently transfer the pressure on the hollow body when pressed by hand against the patient's skin and to distribute it evenly. The cushion ring can be made from any desired deformable and especially elastomeric material, such as rubber or plastic.

The hollow body can also be designed as a single piece with the wound cover element. This can be the case, in particular, for the smaller sizes of wound cover element. A single-piece configuration can furthermore pertain to a product which is assembled from the hollow body, the wound cover element, and the encased absorption body. Here, "single-piece" refers to a one-part design, e.g., a molded piece.

The wound treatment device can be provided with at least one window arranged on the wound cover element and able to be removed or swiveled, on which the mentioned hollow body sits. In this case, the wound cover element has at least one recess to accommodate the window.

A vacuum indicator can be connected or connectable to the valve, by which the patient himself or the doctor can read off the vacuum level and change it if necessary by activating the hollow body or the valve. The vacuum indicator can be part of an external pump. The vacuum producing element itself, i.e., the hollow body, can take on the supplemental function of a vacuum indicator if it is appropriately scaled. For example, the vacuum indicator can be a scaled glass tube with piston, connected directly to the valve.

With the wound treatment device according to the invention, the following kinds of wounds can be treated:
  mechanical wounds such as cuts and puncture injuries, bite wounds, gunshot wounds, abrasions;
  iatrogenic wounds;
  thermal wounds, such as burns;
  chemical wounds, such as acid or alkali burns;
  open wounds; and
  perforating wounds and others.

Some additional selected usage possibilities are listed below:
  as a dressing to treat an edematous or inflammatory altered wound region;
  as a dressing to treat a microbially laden wound surface, by using the suction force to take germs or cell fragments into anaerobic regions of the swollen absorption body;
  as a dressing to remove inflammatory cytokins, matrix metalloproteases, TIMPs, degraded fibronectin (holds the tissue together) or other substances causing chronicity;
  as a dressing to regulate the air humidity, since the absorption body releases the aqueous components back into the air through their vapor pressure;
  as a dressing on top of a primary applied wound spacer grid or a gauze as a secondary dressing having no immediate sheet-like contact with the wound;
  as a dressing beneath a film permeable to water vapor to achieve a breathable dressing;
  as a dressing during a compression therapy; and
  as a dressing during a maggot therapy promoting epithelial cell migration and granulation, in which the larvae of *Lucilia sericata* are used; this involves, in particular, acute and chronic wound infections. Instead of larvae, a substance secreted by the maggots can be used, namely, their saliva.

The benefits of the invention consist, in particular, in that:
  thanks to the use of the encased absorption body, the moist environment within the wound cavity can be maintained;
  the absorption process can be supported by the air evacuation;
  the air evacuation can be done by the patient; it is enough to exert a pressure by hand or finger on the bellows or the ball of the hollow body;
  the absorption body can serve as a storeroom for the wound exudate; the liquids need not be carried away from the wound region; instead, they can be gathered close to the wound; and
  the time and the costs of the wound treatment can be reduced.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

BRIEF DESCRIPTION OF THE DRAWINGS

Sample embodiments of the invention are explained more closely hereafter by means of the drawing. The figures show.

DETAILED DESCRIPTION OF THE INVENTION

Figure 1:
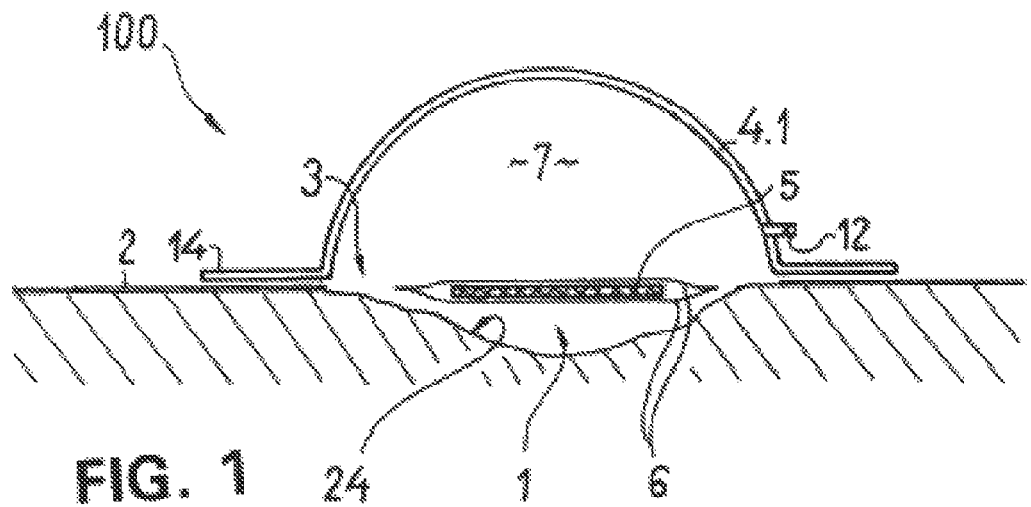
FIG. 1, a wound treatment device with a bell-shaped hollow body, glued onto the skin of the patient, in a schematic representation.
Figure 2:
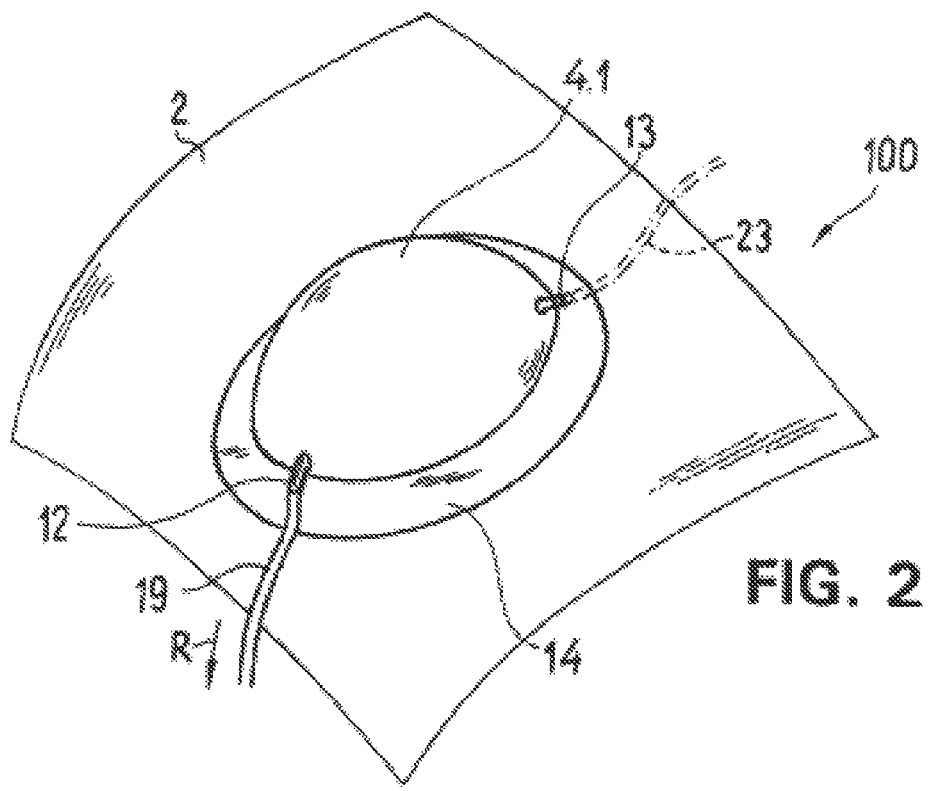
FIG. 2, the wound treatment device per FIG. 1 in a perspective view.

FIGS. 1 and 2 show a first embodiment (reference number 100) of the wound treatment device, consisting of a film-like wound cover element 2, a bell-shaped hollow body 4.1 and an absorption body 5. The hollow body 4.1 is made as a molded piece of polyethylene in the deep drawing process. The wall thickness of the translucent hollow body is 0.8 mm. The spherical molded piece passes into a peripheral flat collar 14, which is glued onto the wound cover element 2 by means of a medically safe adhesive. The wall of the hollow body bounds a cavity 7, which is in direct contact with a wound cavity 1 via an opening 3 made in the wound cover element 2. The wound cavity 1 is defined by a wound surface, designated as 24, and the wound cover element 2.

The hollow body 4.1 is provided with a one-way valve 12, which allows the flow through of air and—if necessary—excess wound secretions, if the hollow body is connected via an additionally provided conduit 19 to a corresponding mechanical or electrical suction device (not shown), in one direction (arrow R). Thus, a return flow from the outside is prevented. Even so, another one-way valve 13 (see FIG. 2) can be provided, with which the pressure inside the hollow body and thus in the wound cavity 1 can be regulated. Medications can be dispensed via a conduit 23, indicated by broken line.

Figure 3:
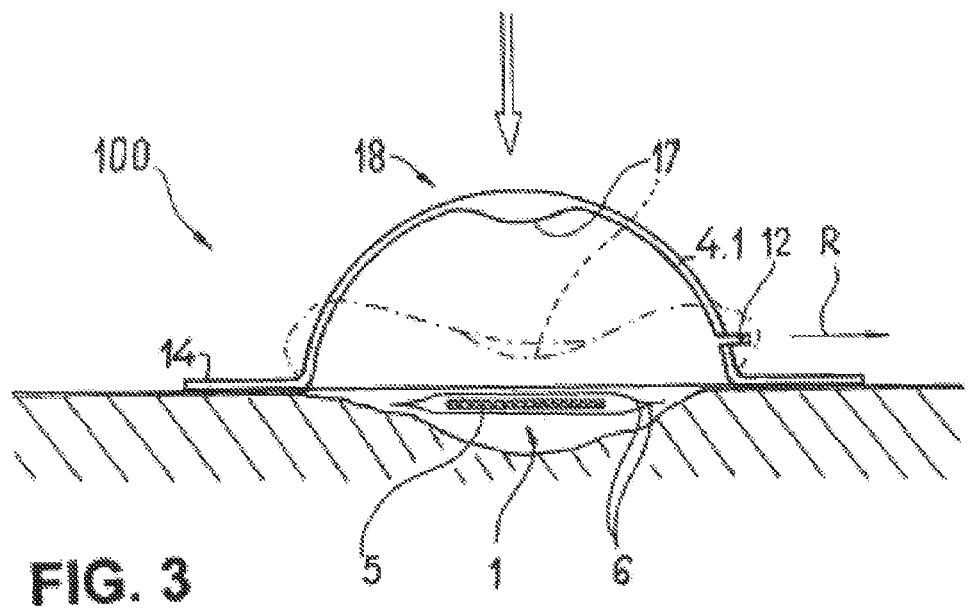
FIG. 3, the wound treatment device per FIG. 1 with a thickening arranged in its apex region, in a schematic representation.
Figure 4:
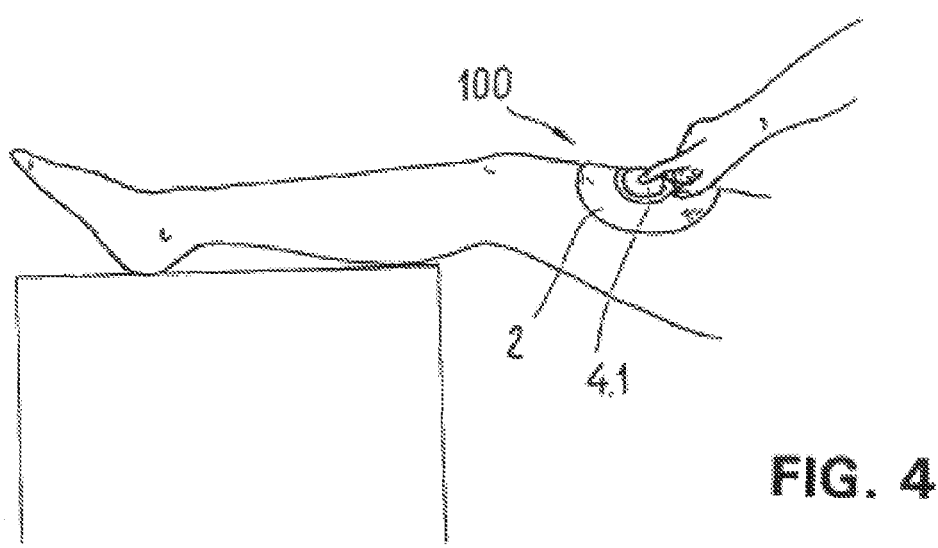
FIG. 4, the wound treatment device per FIG. 1 in use.

FIGS. 1, 3 and 4 shows the wound treatment device 100 in use. First, the opening 3 on the film-like wound cover element 2 is cut out according to the wound size and the wound cover element 2 is glued onto the skin of the patient. The absorption body 5 is laid flat in the wound cavity 1 underneath the wound cover element 2 and only then is the hollow body 4.1 installed with its flat collar 14. FIGS. 1 and 3 show this condition. The absorption body 5 is surrounded by a perforated envelope 6, whose dimensions (width and length, or diameter) are much larger than those of the absorption body. In the present case, the absorption body 5 is around 5.5 cm×5.5 cm in plan view on its flat side and the envelope is around 7.0 cm×7.0 cm in size.

According to FIG. 3, the hollow body 4.1 has a thickening 17 in the region of its apex 18, which can facilitate the deformation of the hollow body when pressing on it by hand, as shown in FIG. 4.

Figure 5:
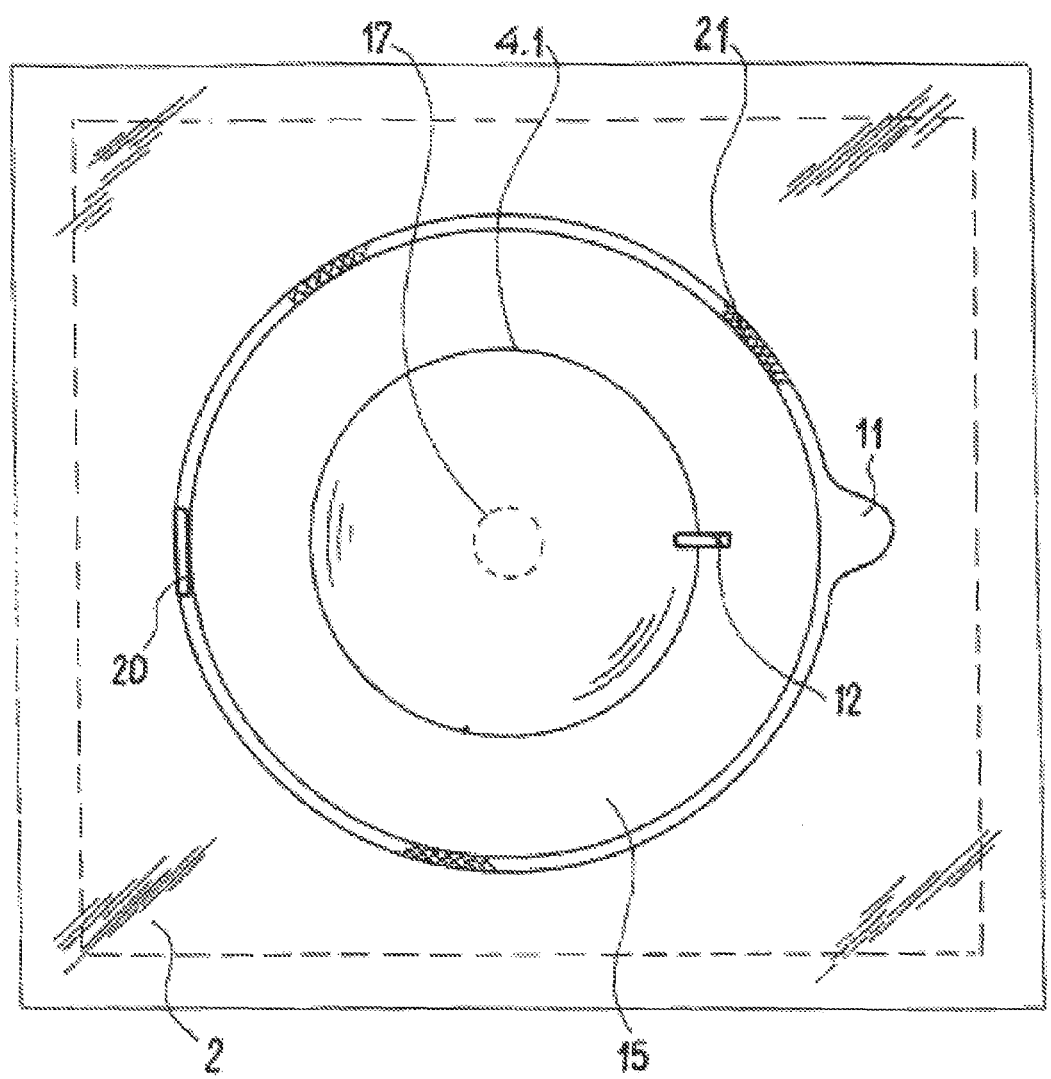
FIG. 5, the wound treatment device per FIG. 1 in a top view of the wound cover element.

The embodiment per FIG. 5 calls for arranging the hollow body 4.1 on a round window 15, which can swivel via a film hinge 20. The window 15 is coated peripherally on its underside with a release glue 21, so that it can be opened and glued back again as needed, for example, in order to take out the swollen absorption body. A pull flap 11 facilitates the handling of the window.

Figure 6:
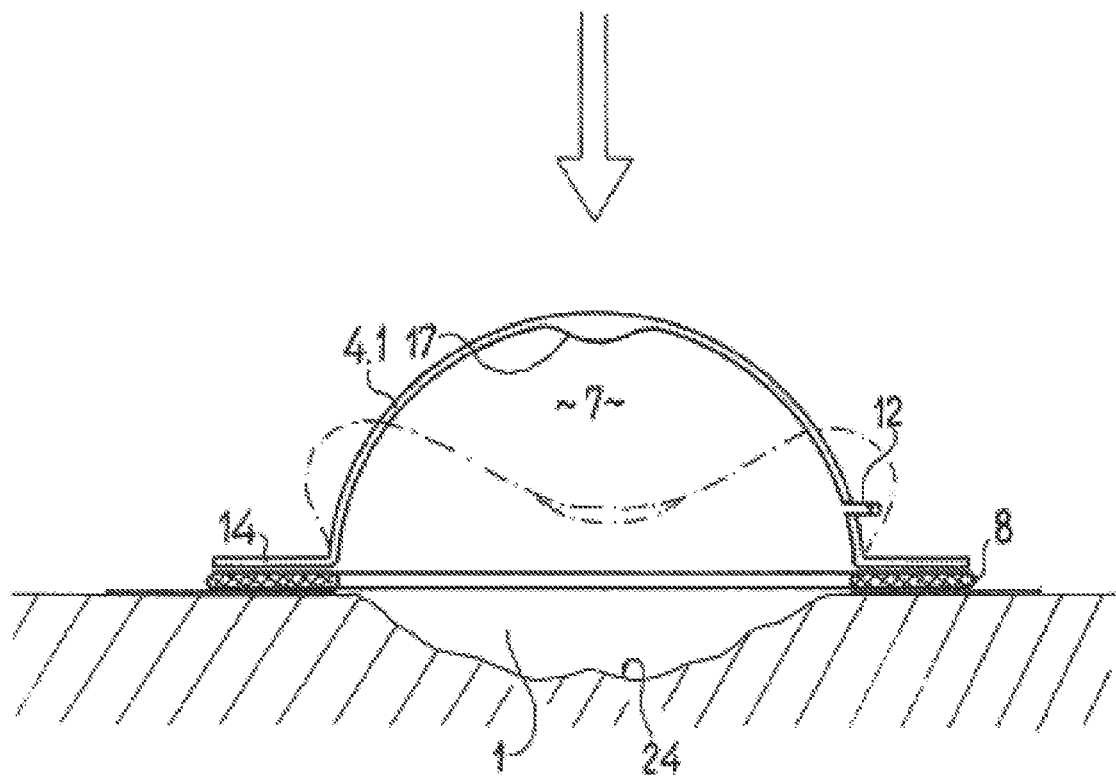
FIG. 6, the wound treatment device per FIG. 1, with a cushion ring, in a schematic representation.
Figure 7:
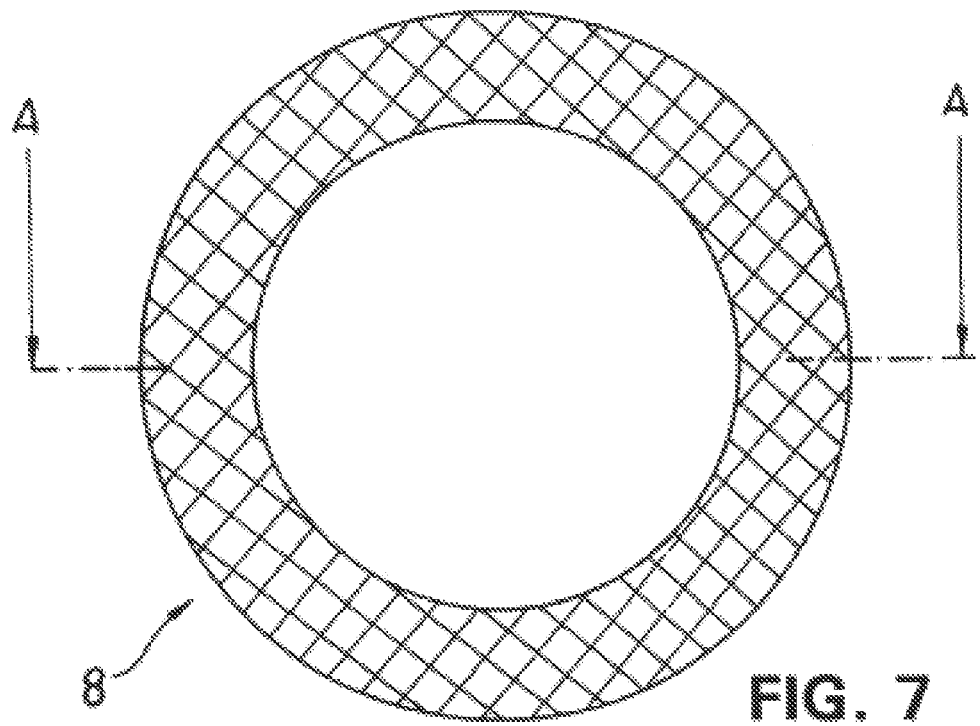
FIG. 7, the cushion ring in top view of its flat side.
Figure 8:
FIG. 8, a cross section A-A per FIG. 7.

The hollow body 4.1, as shown in FIG. 6, can be braced against a cushion ring 8 by its flat collar 14. The cushion ring 8 (see FIGS. 7 and 8) is made from an elastomeric material, which allows the pressing forces exerted by hand to be distributed over its entire surface. It is beneficial that the cushion ring 8 can increase the effective volume of the cavity 7 of the hollow body 4.1.

Figure 9A:
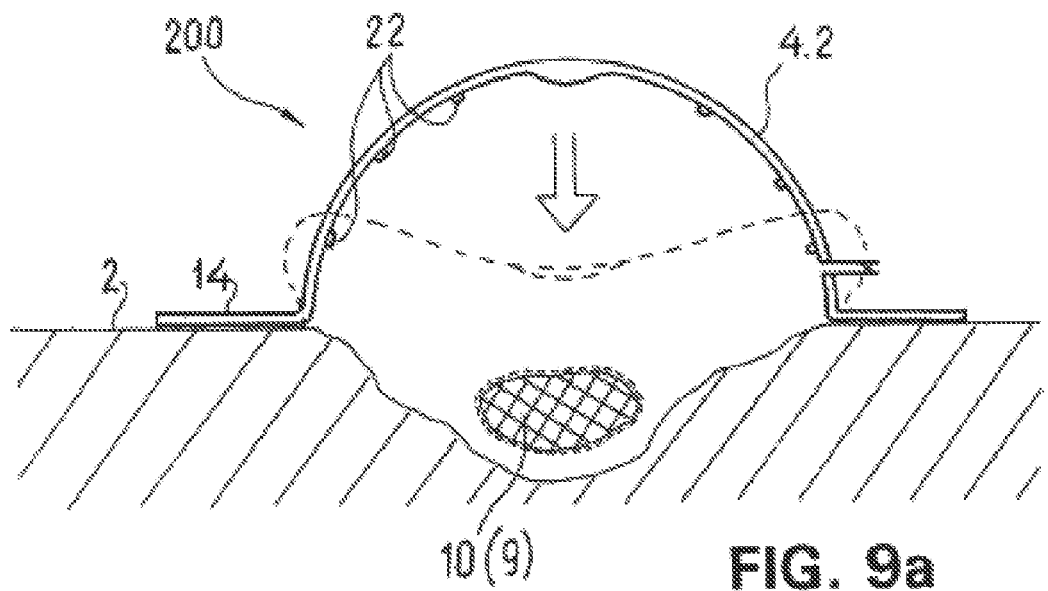
FIG. 9a, a second embodiment of the bell-shaped hollow body, with inward pointing projections, in a schematic view.
Figure 9B:
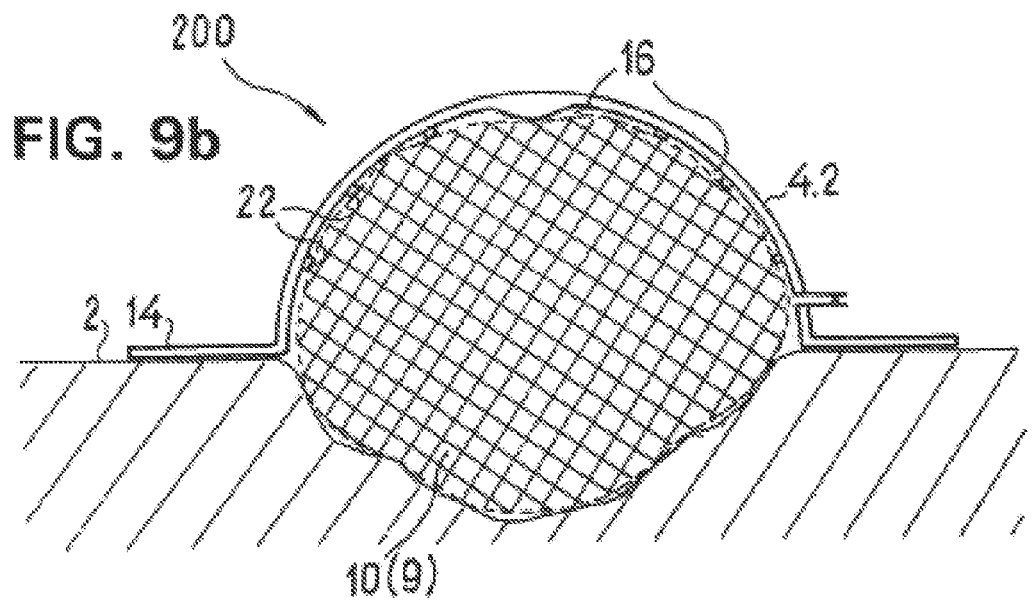
FIG. 9b, the hollow body per FIG. 9a with swollen absorption body.

FIGS. 9*a* and 9*b* show a similar embodiment (designated 200) of the wound treatment device, in which several spacers 22 are provided on the inside of the hollow body 4.2. A perforated pouch 10 with a somewhat lens-shaped absorption body 9 contained therein is laid in the wound cavity 1. When the absorption body 9 swells to its maximum volume (see FIG. 9*b*), the spacers 22 prevent the absorption body 9 from taking up the entire cavity 7, since some free spaces 16 remain between the envelope 6 and the inner surface of the hollow body 4.2, making it possible to dispense liquid medications via the conduit 23 (see FIG. 2) even before removal of the absorption body 9.

Optionally, the absorption bodies 5, 9 can contain a quantity of nanoparticles of silver, copper or zinc, which are useful as antibacterial agents.

Figure 16:
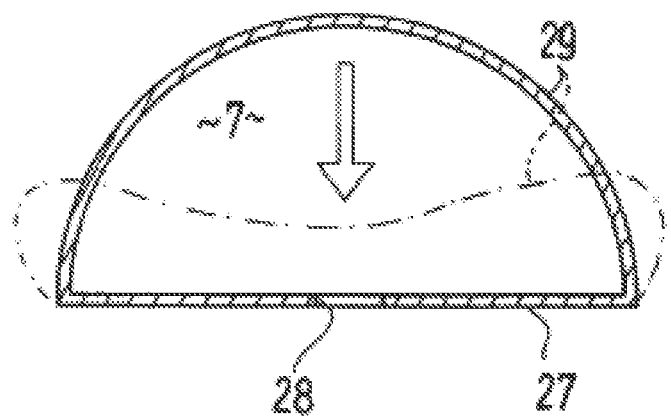
FIG. 16, a hollow body with bottom plate element, likewise in a schematic representation.

FIG. 16 shows a hollow body whose ball-shaped, compressible part 29 passes into a plate-like bottom element 28, on which is arranged an opening 27, situated in the middle, and making contact with the wound cavity 1 (not shown). The bottom element 28 makes possible a uniform distribution of pressure when exerting pressing force by hand.

Figure 10A:
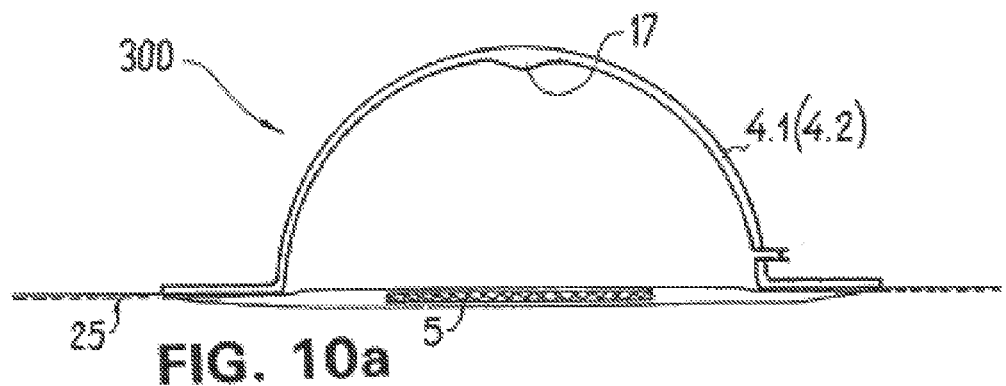
FIGS. 10a to 10c, a further, single-piece embodiment of the wound treatment device, likewise in a schematic representation.
Figure 10B:
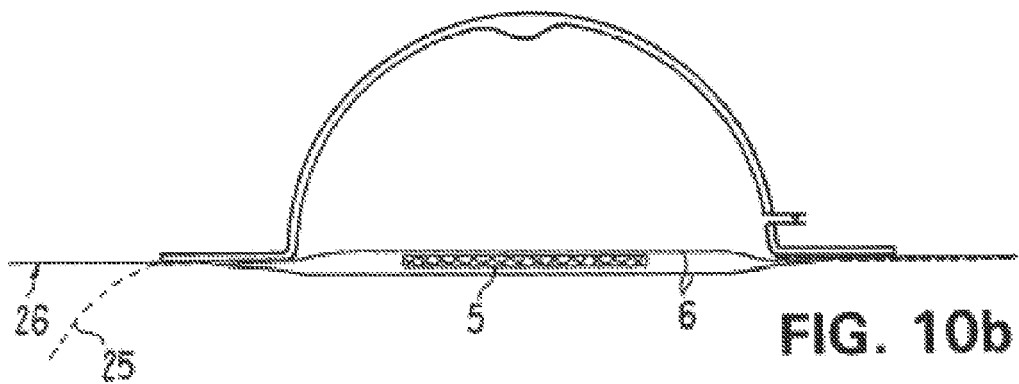
Figure 10C:
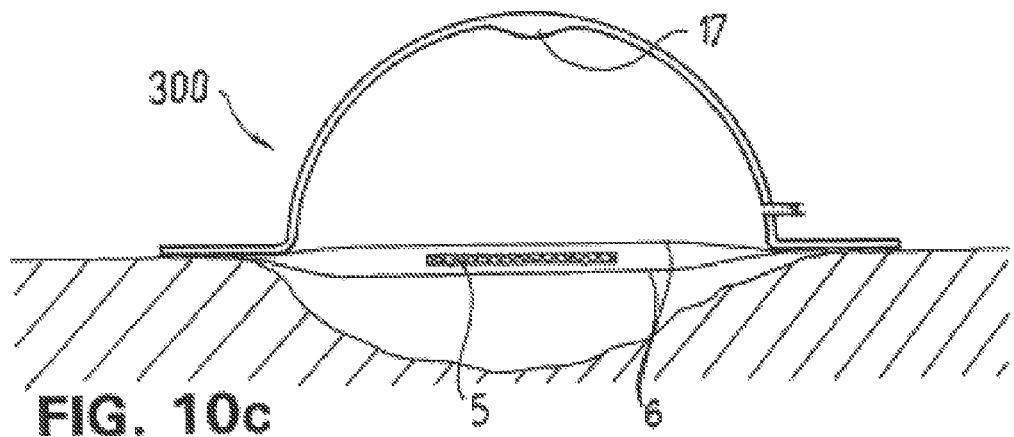

FIGS. 10*a*, 10*b* and 10*c* show a one-piece wound treatment device 300, consisting of a hollow body 4.1 or 4.2 with a film segment of the wound cover element, an absorption body 5 glued to this, and a removable, peripherally arranged, ring shaped protective film 25. The collar 14 of the hollow body 4.1 is firmly glued or welded to the wound cover element. Before putting the wound cover element in place, the protective film 25 is pulled off, so that a glue layer 26 located on the underside of the wound cover element is exposed (see FIG. 10*b*) and the device can be glued onto the patient's skin all around the wound (see FIG. 10*c*). The wound treatment device 300 is designed as a prefabricated disposable product, which can be made in various sizes.

Figure 11A:
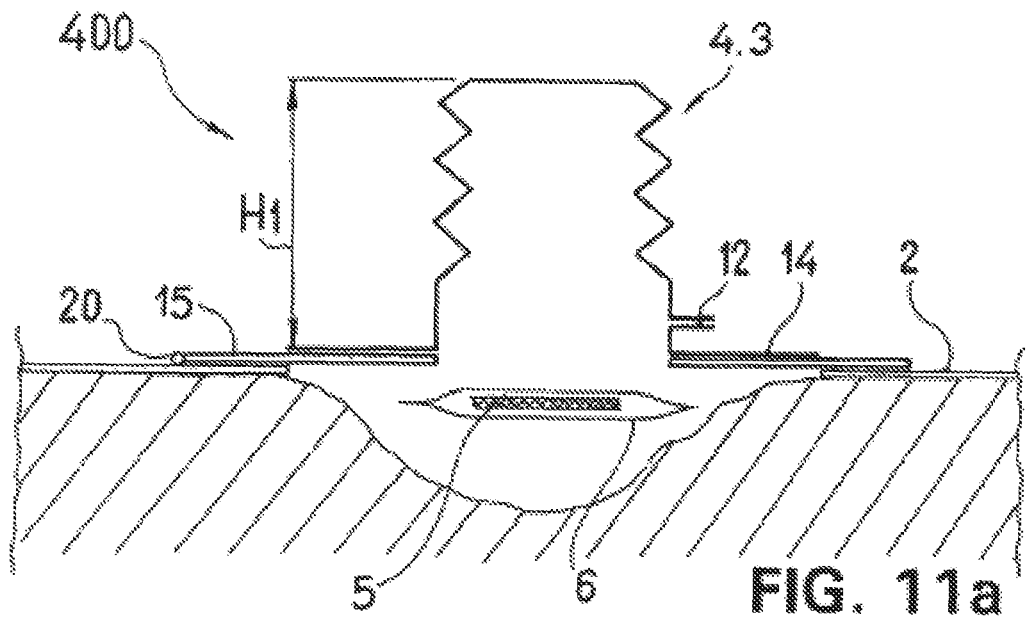
FIGS. 11a to 12, a fourth, bellows-like embodiment of the wound treatment device, in a schematic representation.
Figure 11B:
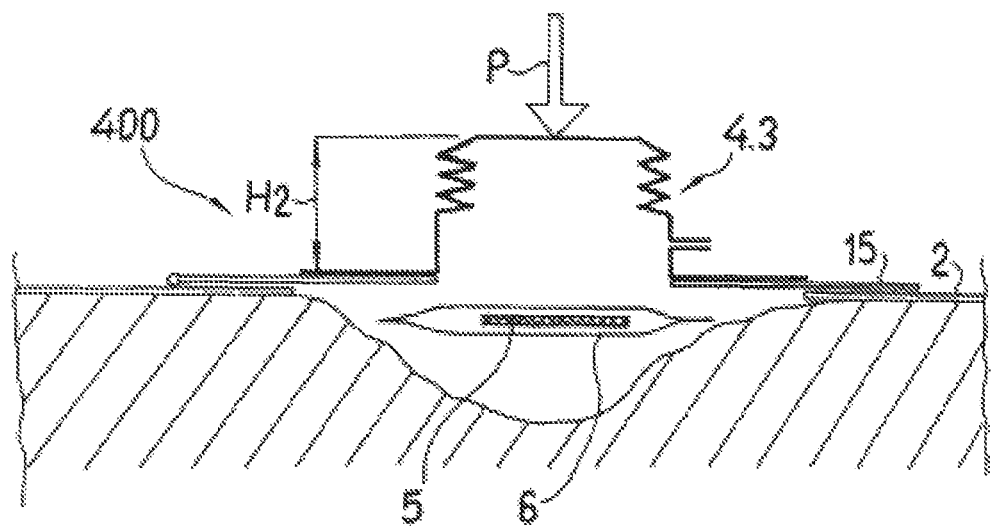
Figure 12:
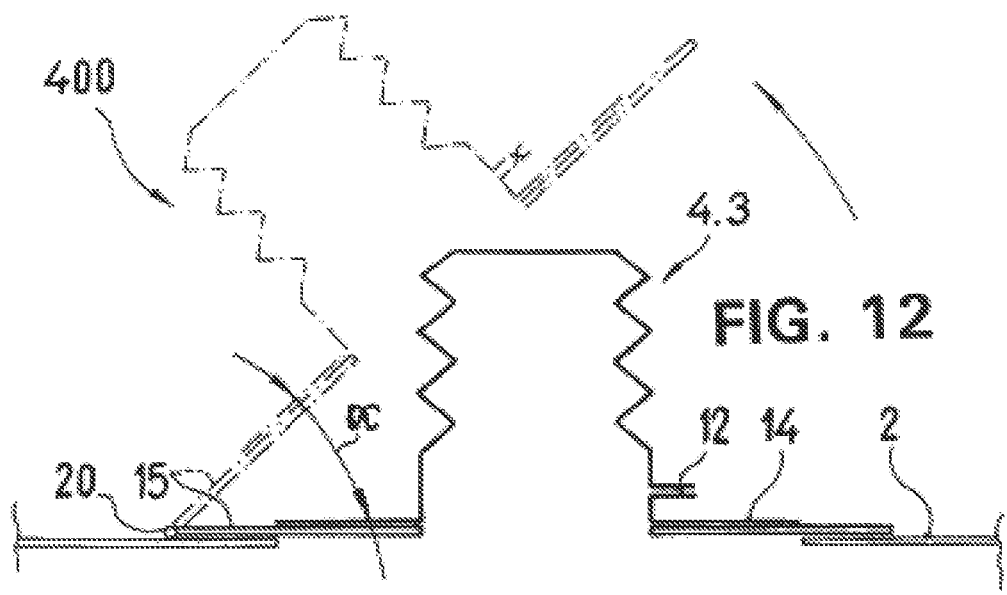

FIGS. 11*a*, 11*b* and 12 show a wound treatment device 400, which is basically similar to that shown in FIG. 5, with the difference that its hollow body 4.3 has the shape of a cylindrical bellows, which can be deformed basically only in one direction, corresponding to a pressing force designated as P (see FIG. 11*b*). The bellows can be compressed very easily by hand or by finger. FIG. 12 shows, in turn, the bellows-like hollow body 4.3 in two positions. The hollow body 4.3 can be swiveled through a very wide angle α by the film hinge 20.

Figure 13:
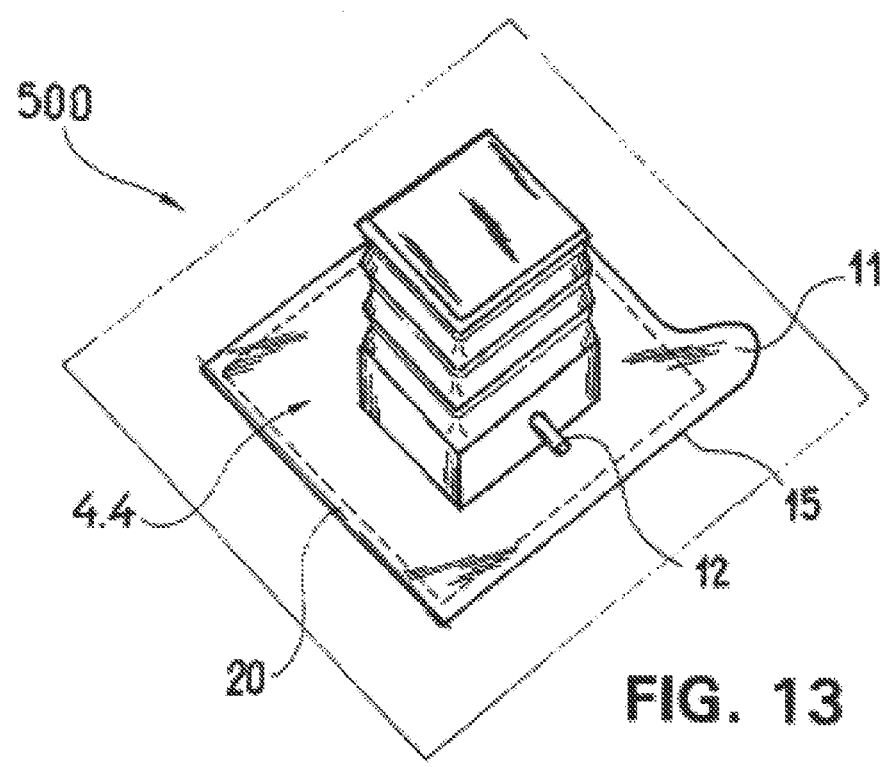
FIG. 13, a wound treatment device with a cuboidal, bellows-like hollow body, in a perspective view.

The embodiment of FIG. 13 is a wound treatment device 500 having a film-like rectangular window 15, on which a cuboidal hollow body 4.4 is arranged. The design principle of the wound treatment device 500 is identical to that of the wound treatment device 400.

Figure 14:
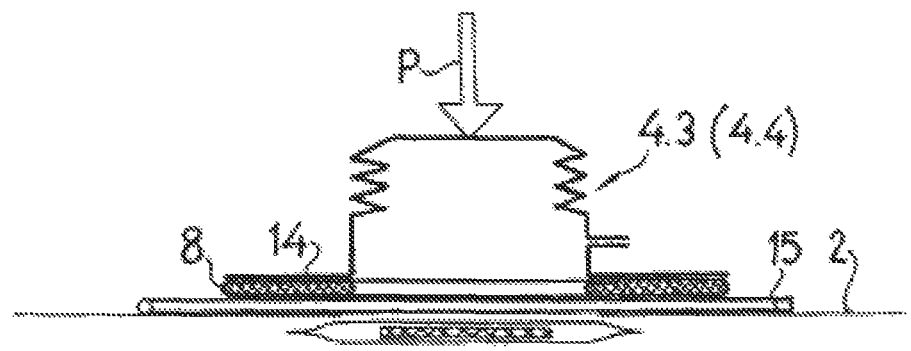
FIG. 14, the wound treatment device per FIG. 11, with a cushion ring, in a schematic representation.

As FIG. 14 shows, the two hollow bodies 4.3, 4.4 can likewise be braced against the cushion ring 8 by their flat collar 14. Preferably, the bellows of the hollow body is configured such that its portion extending from the flat collar 14 has smaller dimensions (diameter or width) than those of the compressible part. This configuration makes it possible to shove the finger of the hand underneath the upper, compressible part and press the bellows with the thumb, without having to exert pressure on the wound cover element 2.

Figure 15:
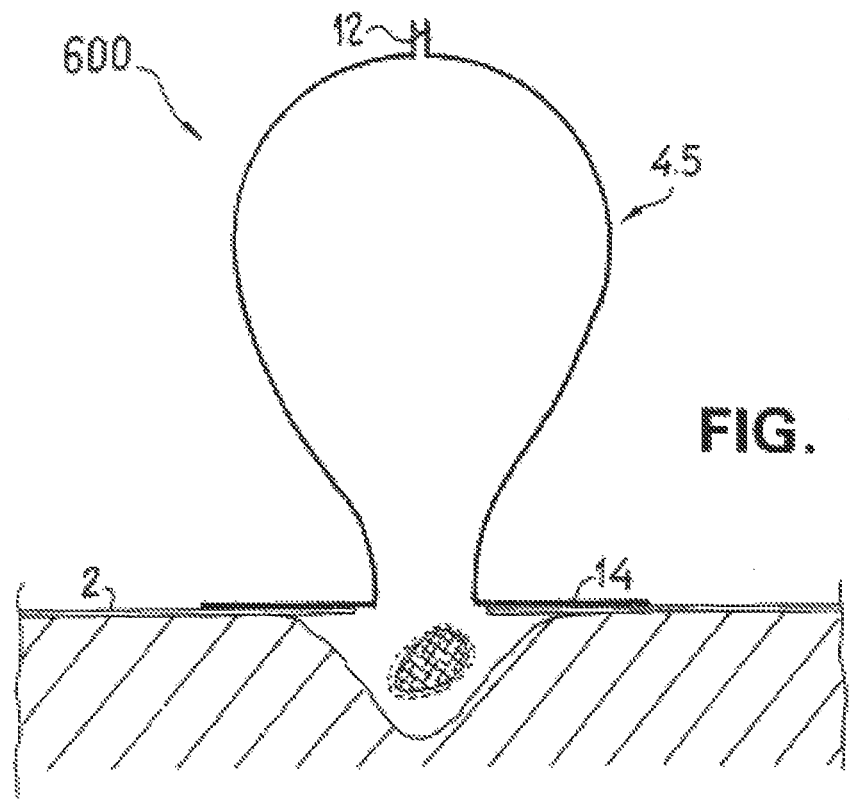
FIG. 15, a wound treatment device with a ball-shaped hollow body, in a schematic representation.

Finally, FIG. 15 shows a wound treatment device 600 whose hollow body 4.5, provided with the flat collar 14, is roughly pear shaped. The one-way valve 12 can be seen in the apex region.

All wound treatment devices 100 to 600 described, and their parts, come in sterile packaging.

TABLE OF REFERENCE SYMBOLS USED IN THE DRAWING FIGURES

Table of reference symbols:

| | |
|---|---|
| 1 | wound cavity |
| 2 | wound cover element |
| 3 | opening |
| 4.1 to 4.5 | hollow body |
| 5 | absorption body |
| 6 | envelope |
| 7 | cavity |
| 8 | cushion ring |
| 9 | absorption body |
| 10 | pouch |
| 11 | pull flap |
| 12; 13 | one-way valve |
| 14 | flat collar |
| 15 | window |
| 16 | space |
| 17 | thickening |
| 18 | apex |
| 19 | conduit (additional) |
| 20 | hinge |
| 21 | release glue |
| 22 | spacer |
| 23 | one-way valve |
| 24 | wound surface |
| 25 | protective film |
| 26 | glue layer |
| 27 | bottom element |
| 28 | opening |
| 29 | part |
| α | angle |
| P | pressing force |
| R | direction |
| 100; 200; 300; 400; 500; 600 | wound treatment device |

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A wound treatment device having at least one elastically deformable vacuum producing element, which can be operated directly by hand, arranged on a film-like wound cover element, which is configured to cover a wound cavity in a patient's body, and which is configured to be connected to the patient's body tubelessly, wherein the vacuum producing element is a hollow body having a cavity that is configured to communicate with the wound cavity via an opening in the wound cover element when the wound cover element is placed on the patient's body, wherein the vacuum producing element generates and maintains a vacuum pressure upon being elastically deformed and released; and wherein the wound treatment device further comprises at least one absorption body that is configured to lie flat in the wound cavity to absorb wound secretions, the absorption body comprising at least one-film-layer of a fleece-like textile material containing cellulose and superabsorbent particles, which is surrounded by a fine-pore, liquid-permeable envelope.

2. The wound treatment device according to claim 1, wherein the hollow body is in a shape selected from the group consisting of a bell, a tray, a bellows, a ball or a pear.

3. The wound treatment device according to claim 1, wherein the hollow body has a collar, which is joined to the wound cover element.

4. The wound treatment device according to claim 1, wherein the hollow body is designed as a single piece with the wound cover element.

5. The wound treatment device according to claim 1, wherein the hollow body is supported against a cushion ring.

6. The wound treatment device according to claim 5, wherein the cushion ring is elastic.

7. The wound treatment device according to claim 1, wherein the wound treatment device is provided with at least one valve.

8. The wound treatment device according to claim 7, wherein the valve is arranged on the hollow body.

9. The wound treatment device according to claim 7, wherein the valve is a one-way valve.

10. The wound treatment device according to claim 1, wherein the absorption body is sheet-like in a non-swollen condition.

11. The wound treatment device according to claim 1, wherein the absorption body has a shape other than sheet-like in a non-swollen condition.

12. The wound treatment device according to claim 1, wherein the envelope has pores whose size does not greatly exceed that of the superabsorbent particles.

13. The wound treatment device according to claim 1, wherein the absorption body:
   contains alginate fibers;
   is sponge-like; or
   is gel-like.

14. The wound treatment device according to claim 1, wherein the absorption body and/or the envelope is enriched with metallic nanoparticles.

15. The wound treatment device according to claim 1, wherein the opening of the wound cover element is covered by a window, wherein the hollow body is arranged on the window, and wherein the window can be removed or swiveled away from the wound cover element.

16. The wound treatment device according to claim 1, wherein the hollow body is provided with a bottom element, and wherein an opening is provided in the bottom element.

17. The wound treatment device according to claim 1, wherein the absorption body contains one or more selected from the group consisting of carboxymethylcellulose, honey, honey derivatives, propolis, pharmaceutically active plant additives, and synthetic high-molecular hyaluronic acid.

18. The wound treatment device according to claim 1, wherein the absorption body is enriched with natural hyaluronic acid.

19. The wound treatment device according to claim 1, wherein the hollow body has a thickening in an apex region that facilitates deformation of the hollow body when the hollow body is pressed toward the wound cavity by hand.

20. The wound treatment device according to claim 19 further comprising a one-way valve that allows air to exit from the cavity in the hollow body when the wound cover element is placed on the patient's body and the hollow body is pressed by hand.

* * * * *